United States Patent
Monsivais

(10) Patent No.: US 11,395,502 B2
(45) Date of Patent: Jul. 26, 2022

(54) FORMULATION FOR IRON SUPPLEMENTS

(71) Applicant: Patrick Monsivais, Greenville, SC (US)

(72) Inventor: Patrick Monsivais, Greenville, SC (US)

( * ) Notice: Subject to any disclaimer, the term of this patent is extended or adjusted under 35 U.S.C. 154(b) by 0 days.

(21) Appl. No.: 14/030,075

(22) Filed: Sep. 18, 2013

(65) Prior Publication Data

US 2015/0079268 A1    Mar. 19, 2015

Related U.S. Application Data

(60) Provisional application No. 61/715,545, filed on Oct. 18, 2012.

(51) Int. Cl.
| | |
|---|---|
| *A23L 27/12* | (2016.01) |
| *A23L 33/16* | (2016.01) |
| *A23L 27/00* | (2016.01) |
| *A23L 27/30* | (2016.01) |
| *A23L 33/155* | (2016.01) |
| *A61K 47/61* | (2017.01) |
| *A61K 33/26* | (2006.01) |

(52) U.S. Cl.
CPC .............. *A23L 27/84* (2016.08); *A23L 27/12* (2016.08); *A23L 27/36* (2016.08); *A23L 33/155* (2016.08); *A23L 33/16* (2016.08); *A61K 33/26* (2013.01); *A61K 47/61* (2017.08); *A23V 2002/00* (2013.01)

(58) Field of Classification Search
CPC .......... A23L 27/12; A23L 27/36; A23L 27/84; A23L 33/155; A23L 33/16; A61K 33/26; A61K 47/61

USPC .......................................................... 426/74
See application file for complete search history.

(56) References Cited

U.S. PATENT DOCUMENTS

| | | | |
|---|---|---|---|
| 6,358,544 B1 * | 3/2002 | Henry, Jr. ............... | A23L 1/302 426/590 |
| 8,287,848 B2 * | 10/2012 | Mehta .................. | A61K 31/122 424/439 |
| 2004/0058034 A1 * | 3/2004 | Mehansho ................ | A23L 2/52 426/74 |
| 2005/0037065 A1 * | 2/2005 | Kirschner ............ | A61K 9/4858 424/456 |

(Continued)

FOREIGN PATENT DOCUMENTS

| | | | | |
|---|---|---|---|---|
| WO | WO 2006130027 A1 * | 12/2006 | ........... | A61K 31/375 |
| WO | WO 2013003947 A1 * | 1/2013 | ............ | A61K 33/26 |

OTHER PUBLICATIONS

Mohie-Eldin et al., A comparison of the magnetic properties of polysaccharide iron complex (PIC) and ferritin 1994, Journal of Magnetism and Magnetic Materials, vol. 135, Issue 1, pp. 65-81.*

(Continued)

*Primary Examiner* — Walter A Moore
(74) *Attorney, Agent, or Firm* — Michael Best & Friedrich LLP

(57) ABSTRACT

An iron supplement nutritional formulation for infants and adults is provided using a non-nutritive sweetener including an extract from monk fruit (*Siraitia grosvenorii*) in combination with a polysaccharide iron complex. The formulation improves the taste and palatability of the supplement, thereby increasing the dosage accuracy within children and infants who tend to spit out or regurgitate other forms of polysaccharide iron complexes.

6 Claims, 1 Drawing Sheet

| Adult Formulation | 5 ml | |
|---|---|---|
| Water (Reverse Osmosis) | 4490 | mg |
| Glycerin | 388.9 | mg |
| Iron (Polysaccharide Iron Complex 48%) | 268.227 | mg |
| Citric Acid | 75 | mg |
| Xanthan Gum | 19 | mg |
| Potassium Sorbate | 15 | mg |
| Natural Raspberry Flavor | 13.9 | mg |
| Natural Grape Flavor | 7.5 | mg |
| Sodium Benzoate | 5 | mg |
| Vitamin D-3 (Cholecalciferol) 100,000 IU/G | 1.25 | mg |
| Siraitia (a.k.a. Momordica or Thladiantha) Grosvenorii (Monk Fruit Aka Lo Han) Fruit Extract | 4 | mg |

(56) References Cited

U.S. PATENT DOCUMENTS

| | | | | |
|---|---|---|---|---|
| 2006/0286188 A1* | 12/2006 | Mower | ................ | A61K 36/185 |
| | | | | 424/777 |
| 2008/0214496 A1* | 9/2008 | Tanner-Baumgartner | ................... | |
| | | | | A61P 25/00 |
| | | | | 514/58 |
| 2009/0197944 A1* | 8/2009 | Ota | ......................... | A61P 27/02 |
| | | | | 514/456 |
| 2009/0280199 A1* | 11/2009 | Russell | ................... | A61P 25/00 |
| | | | | 424/732 |
| 2010/0008865 A1* | 1/2010 | Fayet | ..................... | A61K 33/34 |
| | | | | 424/43 |
| 2010/0151055 A1* | 6/2010 | Riess | ..................... | A23L 1/2366 |
| | | | | 424/679 |
| 2010/0316619 A1* | 12/2010 | Wittke | ..................... | A23L 33/40 |
| | | | | 424/93.45 |

OTHER PUBLICATIONS

Nina Planck, Real Food for Mother and Baby—The Fertility Diet, Eating for Two, and Baby's First Foods, 2009, Bloomsbury USA, First U.S. Edition, pp. 162. (Year: 2009).*

* cited by examiner

| Adult Formulation | | 5 ml |
|---|---|---|
| Water (Reverse Osmosis) | 4490 | mg |
| Glycerin | 388.9 | mg |
| Iron (Polysaccharide Iron Complex 48%) | 268.227 | mg |
| Citric Acid | 75 | mg |
| Xanthan Gum | 19 | mg |
| Potassium Sorbate | 15 | mg |
| Natural Raspberry Flavor | 13.9 | mg |
| Natural Grape Flavor | 7.5 | mg |
| Sodium Benzoate | 5 | mg |
| Vitamin D-3 (Cholecalciferol) 100,000 IU/G | 1.25 | mg |
| Siraitia (a.k.a. Momordica or Thladiantha) Grosvenorii (Monk Fruit Aka Lo Han) Fruit Extract | 4 | mg |

Figure 1

| Pediatric Drops | | 1.0 ml |
|---|---|---|
| Water (Reverse Osmosis) | 894 | mg |
| Glycerin | 77.78 | mg |
| Iron (Polysaccharide Iron Complex 48%) | 31.563 | mg |
| Citric Acid | 9.73 | mg |
| Xanthan Gum | 3.8 | mg |
| Potassium Sorbate | 3 | mg |
| Natural Raspberry Flavor | 2.78 | mg |
| Natural Grape Flavor | 1.5 | mg |
| Sodium Benzoate | 1 | mg |
| Siraitia (a.k.a. Momordica or Thladiantha) Grosvenorii (Monk Fruit Aka Lo Han) Fruit Extract | 0.942 | mg |

Figure 2

FORMULATION FOR IRON SUPPLEMENTS

RELATED APPLICATIONS

This application claims the benefit of U.S. application Ser. No. 61/715,545 filed on Oct. 18, 2012 and which is incorporated herein by reference.

FIELD OF THE INVENTION

This invention is directed towards iron preparations suitable for pharmaceutical and OTC formulations and processes for the preparation thereof. An iron preparation of the invention comprises non-nutritive and dietically sugar free flavoring agents which improve the ingestion rate of iron supplements in infants and young children and improves the flavor and reduces unpleasant aftertaste associated with traditional iron nutritional supplements.

BACKGROUND OF THE INVENTION

This invention relates to improvements in iron nutritional supplements. Iron deficiency is the most common micronutrient deficiency in the world, affecting 1.3 billion people (24% of the world's population). Severe iron deficiency, i.e., iron deficiency anemia, is particularly debilitating, since iron has several vital physiological functions, including: (1) carriage of oxygen from lung to tissues; (2) electron transport within cells; and (3) participation as a co-factor of essential enzymatic reactions in neurotransmission, synthesis of steroid hormones, synthesis of bile salts, and detoxification processes in the liver. Among the consequences of iron deficiency anemia are an increase maternal & fetal mortality, an increased risk of premature delivery and low birth weight, learning disabilities & delayed psychomotor development, reduced work capacity, impaired immunity (high risk of infection), an inability to maintain body temperature, and an associated risk of lead poisoning because of pica.

Iron deficiency anemia commonly affects patients having chronic diseases, such as kidney disease, inflammatory bowel disease, cancer, HIV, and diabetes. Iron deficiency also afflicts mammals after blood loss and females after parturition.

It is well known to treat an iron deficiency with orally administered iron supplements. In general, relatively large doses of oral iron fortificants are needed to achieve a desired therapeutic effect. The absorption of non-heme iron from the gastrointestinal tract varies from 2% to greater than 90% because it is strongly influenced by the iron status of the body, the solubility of the iron salts in aqueous solutions, the integrity of gut mucosa, and the presence of absorption inhibitors or facilitators in ingesta. For example, foods which contain polyphenol compounds and/or phytic acid bind with dietary iron, decreasing the concentration of free iron in the gut and forming complexes that are not absorbed. Cereals such as wheat, rice, maize, barley, sorghum and oats; vegetables such as spinach and spices; legumes such as soya beans, black beans, and peas; and beverages such as tea, coffee, cocoa and wine contain substances that inhibit iron absorption from the gut. Likewise, L-ascorbate and L-cysteine are known to facilitate absorption of ferrous iron.

Oral administration of iron supplements is known to be commonly accompanied by undesirable side effects, including nausea, vomiting, gastric irritation, constipation, and black stools. For these and other reasons, patient noncompliance with dosage regimens is also a common problem. In addition, conventional iron fortificants present safety concerns, since intolerance to conventional iron salts and accidental overdosing of iron is one of the leading causes of hospitalization in adults and children and is a leading cause of death children under the age of six.

Ferric citrate (Chemical Abstracts Registry No. 12338-05-8) is an iron(III) citrate salt composed of ferric iron and citrate ions in an undefined molecular composition. Ferric citrate is used as an iron fortificant and hematinic agent. [*The Merck Index*, 14$^{th}$ Ed, M. J. O'Neil, P. E. Heckelman, C. B. Koch, K. J. Roman, Eds. Merck & Co., Inc., Whitehouse Station, N.J., 2006, Monograph No. 4021, page 687.]

Ferric iron complexed to a low-molecular-weight polysaccharide, such as a polysaccharide prepared by extensive hydrolysis of starch, is commonly used as an oral hematinic. Commercial preparations of polysaccharide iron complex (PIC) frequently have high alcohol content and/or have unpleasant tastes, both of which can lead to complications. For infants and young children the alcohol content can interfere with normal physiological functions. For all patients, unpleasant taste can lead to nausea and vomiting which creates uncertainty as to dosage requirements. Infants, in particular, will spit out the PIC formulations, making dosage calculations imprecise and can lead to iron poisoning if a care giver provides too great a dosage of PIC.

There is a need for an iron nutritional supplement preparation having no alcohol and incorporating sweeteners that will not affect blood glucose levels and that effectively masks the unpleasant iron tastes and have fewer ingestion-related side effects than traditional PIC formulations. Accordingly, there remains room for improvement and variation within the art.

SUMMARY OF THE INVENTION

It is one aspect of at least one of the present embodiments to an iron supplement nutritional formulation for infants and adults which can be provided using a non-nutritive sweetener including an extract from monk fruit. Monk fruit (Lo Han or Luo Han Guo) (*Siraitia grosvenorii*) is an herbaceous perennial vine of the Cucurbitaceae (gourd) family. Use of the sweetener is of value in that the sweetener has a better taste. The formulation's taste is better suited for use with infants and young children who may object to other formulations which have an unpleasant taste which tend to induce vomiting and a gag reflex. The use of a monk fruit sweetener does not disrupt blood glucose levels and allows for a formulation of an iron supplement that avoids alcohol. One suitable source for monk fruit is available under the trademark brand Purefurit™ having a mogroside V (50%) extract obtained from the monk fruit. The sweetener is available from Tate and Lyle PLC London, United Kingdom.

The various formulations are useful for providing oral iron supplements having the listed ingredients. The formulations also have utility as to formulations consisting essentially of the ingredients as set forth in the attached formulas.

A further aspect of at least one embodiment of the present invention is to provide for a female oral contraceptive supply in which the traditional 7 day of placebo pills are replaced by pills having a PIC iron supplement.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

FIGS. 1 and 2 are charts setting forth formulations for a polysaccharide iron complex supplement.

DESCRIPTION OF THE PREFERRED EMBODIMENT

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment.

It is to be understood that the ranges and limits mentioned herein include all ranges located within the prescribed limits (i.e., subranges). For instance, a range from about 100 to about 200 also includes ranges from 110 to 150, 170 to 190, 153 to 162, and 145.3 to 149.6. Further, a limit of up to about 7 also includes a limit of up to about 5, up to 3, and up to about 4.5, as well as ranges within the limit, such as from about 1 to about 5, and from about 3.2 to about 6.5. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

As set forth in the FIGS. 1 and 2, PIC-containing formulations are provided that have been found to offer numerous advantages to traditional PIC complex formulations. As set forth in the Figures, the formulations utilize Monk fruit derived sweeteners. It has been found that the use of Monk fruit sweeteners can mask the unpleasant taste of the PIC as opposed to the use of other sugars, natural sweeteners or artificial sweeteners. In addition, the formulations set forth the optional inclusion of other natural flavorings derived from grape and raspberry which also help with palatability and taste. It has been found that the formulations significantly improve the palatability of the PIC containing formulas compared to formulations using other sweeteners.

The improved taste may be of critical importance in terms of a user retaining the supplied dosage. Young children have been found to more readily swallow the full dose, because of the enhanced taste. It has been problematic for parents and child care providers to accurately dose children who spit out and do not swallow the full dose. For young infants in particular, toxicity of too much iron can be of great concern if multiple doses are delivered which overcompensate for the amount a child may have spit out.

The improved taste also avoids gag reflex activation and vomiting that can occur with all age patients using other formulations. Again, such side effects make it difficult to accurate deliver safe and therapeutic amounts of an iron supplement.

Additionally, the formulations do not include any alcohol or alter blood glucose levels. The use of an alcohol-free formulation may be of critical importance for some patients. In young infants and diabetics for instance, even small amounts of alcohol can adversely affect the user. Such side effects are avoided by the present formulations.

The formulation in FIG. 1 is based upon a final volume of 5 ml. The formulation in FIG. 2 is based upon a final volume of 1.0 ml. The specific amounts for each ingredient provides for an effective amount of each ingredient. It is understood that amounts of various ingredients can be varied or even removed while still providing an effective formulation. Similarly, a substitution of equivalent ingredients or inclusion of additional elements such as a thickener, can be provided and would fall within the scope of the present disclosure and invention as set forth in the claims.

An infant formulation as seen in FIG. 2 has substantially about 3.00% of Monk fruit extract as a weight percent in comparison to the amount of PIC. The adult formulation in FIG. 1 has substantially about 1.50% Monk fruit extract in comparison to the amount of PIC. The additional amount of Monk fruit in the infant formulation was added to improve the flavor profile and taste for infants and young children. Lesser amounts are needed in an adult formulation in order to provide a formulation that is still palatable to adults. Additionally, the adult formulation includes Vitamin D-3 which facilitates the absorption and utilization of iron by adults.

The formulations disclosed above can also be used in treating menstrual-associated anemia. If desired, a pill variant of the formulations can be supplied as part of the placebo's supply of pills within a monthly doseaging package of female contraceptives. Alternative formulations of PIC could be used to provide a target iron value of between about 15 mg elemental iron to about 50 mg elemental iron. Such iron formulations can include Polysaccharide-iron complex, Heme iron, Iron salts, Ferrous Sulfate, Ferrous Gluconate, Ferrous Fumarate, Iron Dextran, Carbonyl iron, Ferrous glycine sulfate, and combinations thereof. Inclusion in the placebo pills can provide a timely supplement of iron to counter the menstrual associated anemia some women experience.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

That which is claimed:
1. An iron nutritional supplement comprising:
   an aqueous composition of an oral dose of an iron supplement, wherein the oral dose is in a volume of 5 ml, the aqueous composition comprising a mixture of an effective amount of monk fruit extract to mask a bitter taste of iron, and a polysaccharide iron complex, wherein the weight % of monk fruit extract to mask the bitter taste of the polysaccharide iron complex is between about 1.5% to about 3.0% relative to the weight amount of a polysaccharide iron complex, the polysaccharide iron complex being present at a concentration between about 3.0% to 5.1% by weight of the aqueous composition.

2. The supplement according to claim 1 wherein the amount of monk fruit is present at a percentage by weight of between about 0.08% to about 0.09% the aqueous composition.

3. An iron nutritional supplement of an oral dose of an iron supplement, wherein the oral dose is in a volume of 5 ml or 1.0 ml, the iron nutritional supplement comprising a liquid formulation having a mixture of monk fruit extract and a polysaccharide iron complex where the ratio of monk fruit extract to polysaccharide iron complex ranges from about 1:30 parts by weight to about 1:60 parts by weight and wherein the ratio of monk fruit extract to polysaccharide iron complex is sufficient to mask a bitter taste of iron present in the polysaccharide iron complex, the polysaccharide iron complex being present at a concentration between about 3.0% to 5.1% by weight of the liquid formulation.

4. The iron nutritional supplement according to claim 3 wherein the polysaccharide iron complex is at least about 5.0% by weight of the liquid formulation.

5. An iron nutritional supplement comprising:

an aqueous composition of an oral dose of an iron supplement, wherein the oral dose is in a volume of 1.0 ml, the aqueous composition comprising a mixture of an effective amount of monk fruit extract to mask a bitter taste of iron, and a polysaccharide iron complex, wherein the weight % of monk fruit extract to mask the bitter taste of the polysaccharide iron complex is about 3.0% relative to the weight amount of a polysaccharide iron complex, the polysaccharide iron complex being present at a concentration between about 3.0% to 5.1% by weight of the aqueous composition.

6. The supplement according to claim 5, wherein the amount of monk fruit is present at a percentage by weight of between about 0.08% to about 0.09% the aqueous composition.

* * * * *